United States Patent [19]

Nitzan et al.

[11] Patent Number: 4,848,358

[45] Date of Patent: Jul. 18, 1989

[54] METHOD FOR EXAMINING THE VESTIBULAR SYSTEM AND A HEAD HOLDER THEREFOR

[75] Inventors: Meir Nitzan, Bet El; Joseph Elidan, Jerusalem; Sharon Freeman, Jerusalem; Haim Sohmer, Jerusalem, all of Israel

[73] Assignee: Yissum Research Development Company of the Hebrew University of Jerusalem, Jerusalem, Israel

[21] Appl. No.: 92,928

[22] Filed: Sep. 4, 1987

[30] Foreign Application Priority Data

May 9, 1986 [IL] Israel ..................................... 79948

[51] Int. Cl.$^4$ ............................................. A61B 19/00
[52] U.S. Cl. .................................... 128/740; 128/782; 269/328
[58] Field of Search .................... 269/328; 128/132 R, 128/133, 136, 303 B, 740, 782, 644; 378/20, 68, 177, 179, 195, 208

[56] References Cited

U.S. PATENT DOCUMENTS 4,465,069  8/1984  Barbier ........................... 128/303 B
4,602,622  7/1986  Bar et al. ......................... 128/303 B

FOREIGN PATENT DOCUMENTS

WO83/03534 10/1983 PCT Int'l Appl. .
2135581 9/1984 United Kingdom .

OTHER PUBLICATIONS

Elidan et al., "Vestibular Evoked Response", Annuals of Otology, etc., May-Jun. 1984, vol. 93, No. 3, pp. 257-261.

Primary Examiner—Max Hindenburg
Assistant Examiner—Randy Citrin
Attorney, Agent, or Firm—Millen, White & Zelano

[57] ABSTRACT

A head holder for holding the head of a human subject while imparting to it an acceleration. The holder comprises a helmet-like member at least partly surrounding subject's head, which helmet-like member is adapted to be set in motion by drive means and is provided with at least one head-clamping member appliable to selected locations on the subject's head. The head-clamping member is adapted to transfer the accelerating force produced by the drive means to the head. The arrangement being such that an effective component of the accelerating force applied by the head-clamping member to the head via selected locations thereon acts on the skull bone underneath the locations. A method for examining the vestibular system of a human subject is also described.

8 Claims, 6 Drawing Sheets

METHOD FOR EXAMINING THE VESTIBULAR SYSTEM AND A HEAD HOLDER THEREFOR

The present invention relates to a head holder for holding the head of a human subject while imparting to it an acceleration, in particular for the purpose of examining and testing of the human vestibular system. It further relates to a method for examining and testing this system.

There exist several tests of vestibular function in the evaluation of vertigo, which is one of the most common complaints in clinical medicine, but none of these tests can localize the site of lesion, i.e. differentiate between end-organ lesion (vestibular labyrinth), a vestibular nerve lesion and a more central lesion in the vestibular pathways.

The vestibular tests which are in routine clinical use today are:

1. Bithermal Caloric Test: The vestibular system is stimulated by irrigation of both external ear canals with hot and cold water.
2. Rotational Tests: Vestibular stimulation is achieved by rotating the subject in a chair (angular acceleration up to $200°/sec^2$ for a few seconds).

In both tests the response is a reflex rhythmic eye movement (nystagmus) which is either observed or recorded. It is evident that this is an indirect way of studying the vestibular system.

The routine rotational stimuli and the caloric stimuli cannot be used for the generation and recording of an evoked response because of the extended duration of stimulation. This prevents synchronous activation of a sufficient number of nerve fibers so that it is not possible to record clear, sharp compound action potentials.

A method has been developed for producing and recording evoked responses from the vestibular pathways of experimental animals, which involves imparting high angular acceleration ($2000°$ to $30000°/sec^2$) to the entire animal. While such accelerations can be easily attained with relatively small animals such as rats, cats, or the like, humans whose bodies have a much higher moment of inertia, would require very powerful (and expensive) stepping motors to be accelerated at such rates. Furthermore, the methods used for the rigid holding of the animal, in particular of the animal's head, are definitely not appropriate for humans.

A further disadvantage of the known methods resides in the fact that none of them specifically addresses the receptors for linear acceleration in the inner ear, i.e., the maculae of the utricle and the saccule.

It is one of the objects of the present invention to overcome the above-described difficulties and to provide a head holder suitable for human subjects that would permit the application of angular as well as linear accelerations of the above-indicated magnitudes only to the subject's head which, being the site of the vestibular system, is in fact the only member of the body, the physical motion of which would stimulate this system and, thus, the only member that needs to be moved to evoke responses from this system, and which, on the other hand, has a moment of inertia small enough to be overcome by a power-source of reasonably small size and output.

This the invention achieves by providing a head holder for holding the head of a human subject while imparting to it an acceleration, comprising:

a helmet-like member at least partly surrounding subject's head, which helmet-like member is adapted to be set in motion by drive means and is provided with at least one head-clamping member appliable to selected locations on the subject's head, said head-clamping member being adapted to transfer the accelerating force produced by said drive means to said head, the arrangement being such that an effective component of the accelerating force applied by said head-clamping member to said head via selected locations thereon acts on the skull bone underneath said locations.

The invention further provides a method for examining the vestibular system of a human subject, comprising the steps of:

providing a head holder adapted to be set in motion by drive means;

introducing the subject's head into said head holder using head-clamping members appliable to selected locations on the subject's head;

imparting solely to the subject's head an acceleration of predeterminable magnitude in such a way that an effective component of the accelerating force applied by said head-clamping members acts on the skull bone underneath said head locations;

measuring the electrical signals generated by the excitation of the vestibular nerve and pathways resulting from said accelerations, processing said signals as measured, and evaluating said processed signals.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 defines the angular-acceleration planes referred to in the specification;

Figure 1:
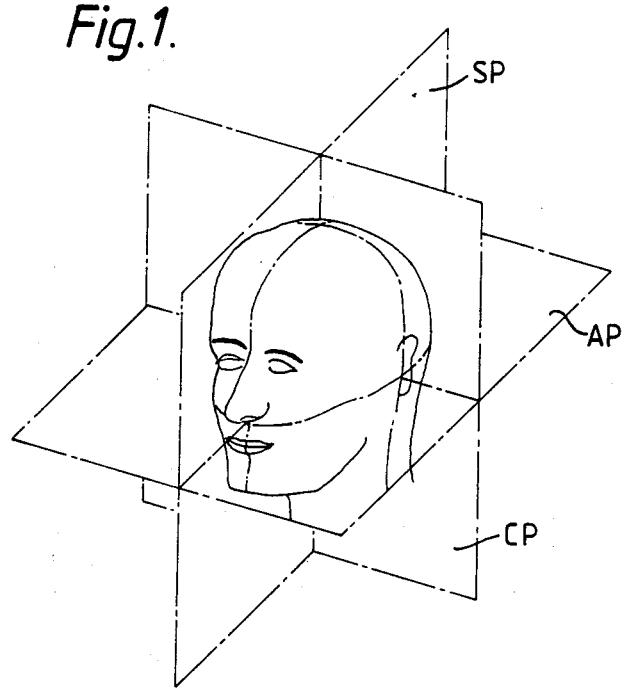
Figure 2:
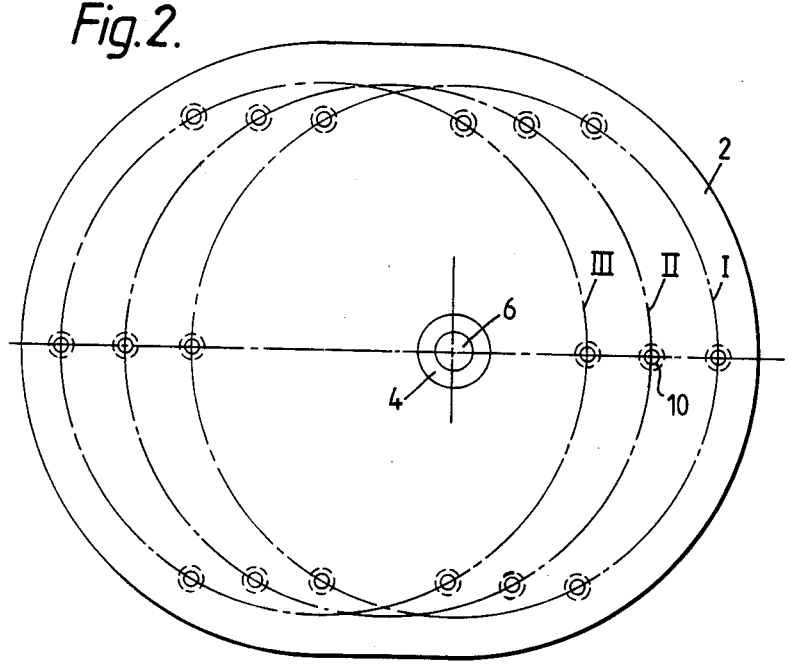
FIG. 2 is a frontal view of the base plate of the head holder according to the invention.
Figure 3:
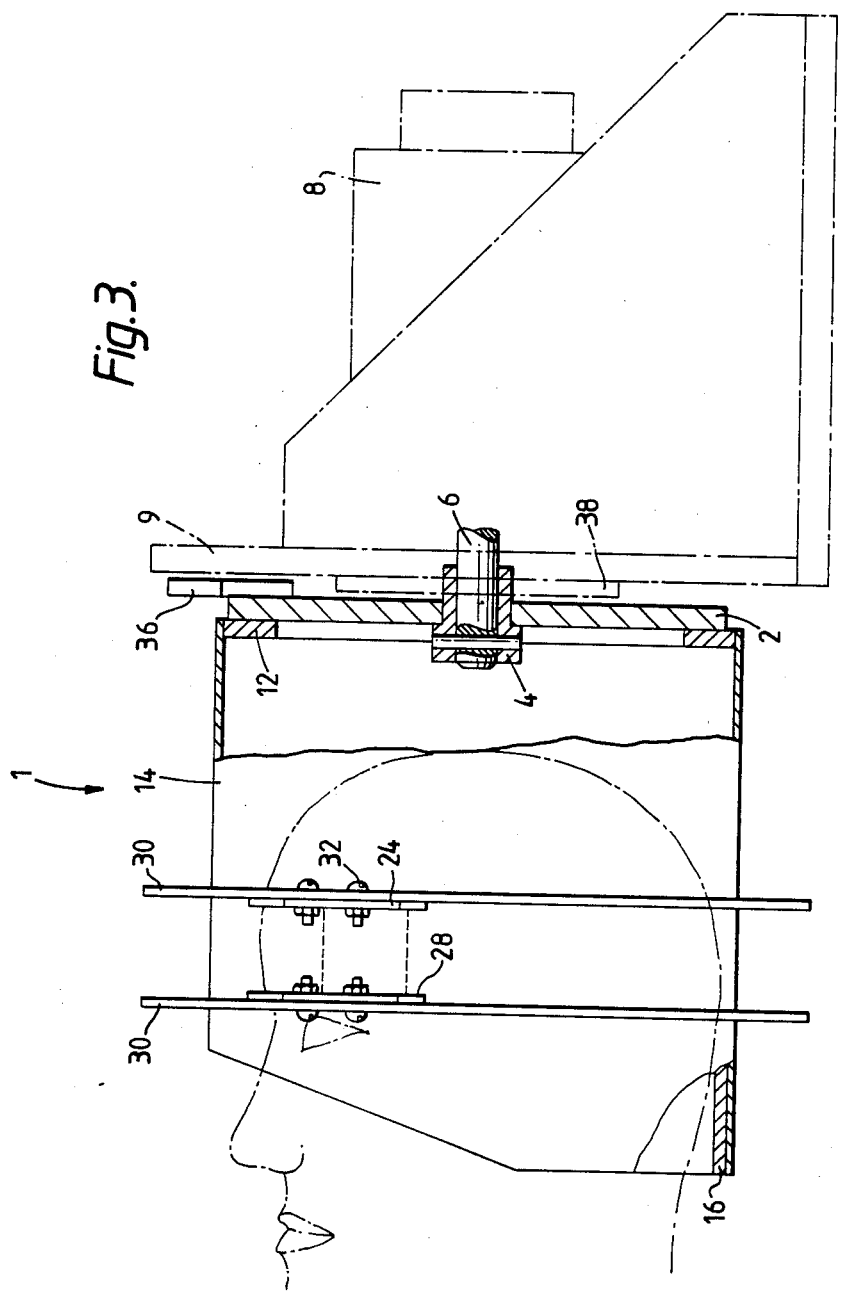
FIG. 3 is a side view of a head holder as connected to a stepping motor.
Figure 4:
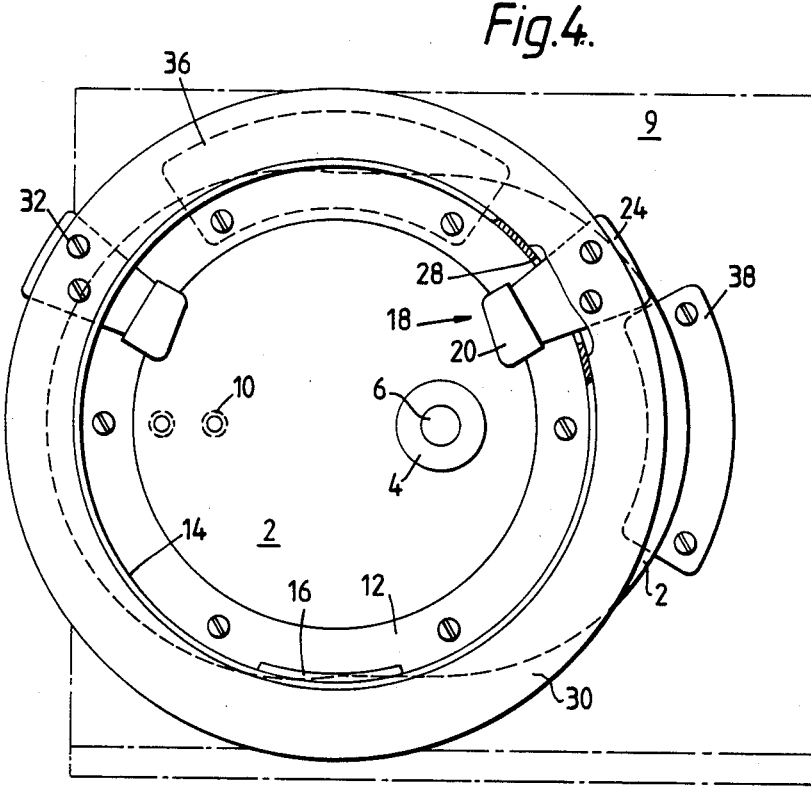
FIG. 4 is a head-on view of the head holder.
Figure 5:
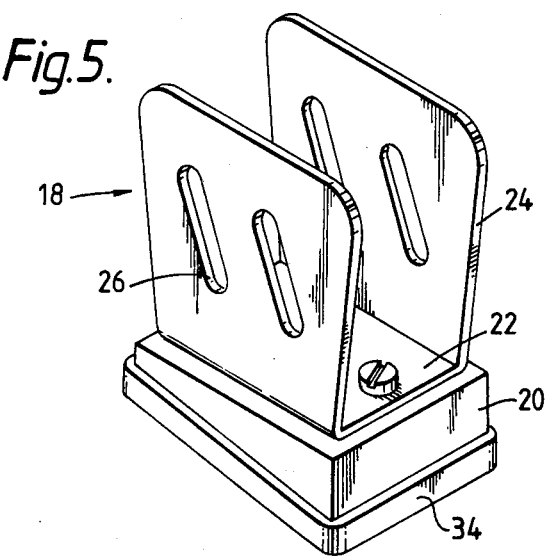
FIG. 5 is a perspective view of one of the head-clamping members.

Referring now to the drawings, there is seen in FIG. 1 a schematic representation of the planes in which a subject's head can be angularly accelerated with the aid of the head holder according to the invention: the axial plane AP, in which the head is shaken as in negation; the coronal plane CP, in which the head is shaken from side to side, and the sagittal plane SP, in which the head is shaken as in assent. It should also be understood that none of the three planes mentioned is unique or singular. Thus, any plane parallel, e.g., to the coronal plane indicated is also considered a coronal plane.

The head holder 1 according to the invention is illustrated in FIGS. 2 to 5. There is seen a base plate 2 of a somewhat elongated form as clearly shown in FIG. 2, and provided with a boss 4 located off center, by means of which boss the base plate 2 can be fixedly attached to the output shaft 6 of a source of rotary power, in this case a stepping motor 8, mounted on a bracket 9, details about which motor—inasmuch as it affects the function of the head holder—will be given further below. There is further seen a plurality of threaded holes 10 arranged on three different hole circles I, II and III, of equal diameters, but mutually offset centers. Hole circle I is concentric with the motor shaft 6, hole circle II is somewhat eccentric with respect to the shaft 6, and hole circle III is even more eccentric. On each of these circles are located the same member of equally spaced holes 10, in this particular embodiment, six.

These holes 10 serve to fixedly attach to the base plate 2, in any of the positions defined by the circles I, II or III, a flange 12 which in turn is rigidly connected to a crown- or helmet-like member 14, into which, as will be explained in greater detail further below, the subject's head is introduced, resting on a rubber pad 16 and immobilized relative to the helmet by means of clamping members 18. The latter, as clearly seen in FIG. 5, consist of a prismatic, slightly tapering pressure pad 20 attached to the web portion 22 of a U-profile, the wing portions 24 of which are provided with elongated holes 26. These wings 24 are pushed through slots 28 in the helmet 14 and, after having been positioned at, and pressed onto, the appropriate portions of the subject's head (see FIGS. 6 or 7), are locked to the helmet 14 with the aid of a pair of flanges 30 that are part of the helmet 14, to which flanges the wings 24 are clamped by means of screws 32. The flanges 30 are obviously provided with a plurality of holes and slots 28 (not shown) to facilitate attachment of the clamping members 18 in various peripheral positions.

The pad 20 is advantageously provided with a lining 34, for which a plastic material known as "orthopaedic plastic" has been found most suitable, as it has a very low softening temperature, is easily shaped when soft, hardens in the range of room and body temperatures and, if need be, can be adapted to the particular features of a subject's skull.

Further provided are safety features in the form of a movable stop 36, permanently attached to the base plate 2, and two stationary stops 38, one on either side of the movable stop 36, permanently attached to the motor bracket 9 (only one stationary stop 38 is shown).

In order to fully appreciate certain characteristic features of the present invention it is necessary to understand some details of the experimental procedure.

Figure 6:
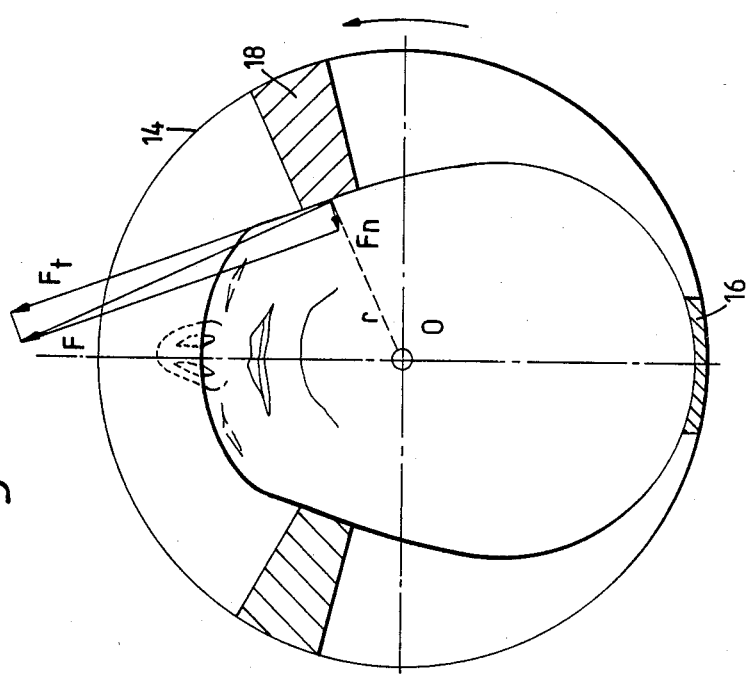
FIG. 6 illustrates the force acting on the head when the helmet is mounted concentrically with respect to the stepping-motor shaft.

As has already been explained, it was found that vestibular evoked responses could be produced by application, to the subject's head only, of a series of consecutive, substantially identical, acceleratory stimuli in the form of impulses of angular-acceleration episodes of the order of $1000°–30000°/sec^2$ over a range of about $1°–3°$, each episode lasting for a few milliseconds. To this end, as already mentioned, the subject's head is introduced into the helmet 14 and immobilized relative to the latter by means of the clamping members 18 in a manner best understood from the schematic drawing of FIG. 6, in which the solid line indicating the shape of the human skull is in fact the outline of a cross section at the height of the temporal bones, slightly above the zygomatic arches. The problem of transferring the acceleration force F from the head holder via the clamping members 18 to the subject's head is that this force is substantially tangential, i.e., normal to the radius r at the point of contact and, as can be seen in FIG. 6, lies very nearly in the plane of the temporal bone. As a consequence, most of the force F is transmitted to the head via the skin overlaying the bone, in the tangential direction, as $F_t$. Now, since the skin is only loosely connected to the skull, most of $F_t$ will be taken up by this looseness of the skin, considering the small amplitude of the angular "jerk" (e.g., $1°–3°$), while the normal component $F_n$, i.e., the only component contributing to the rotational movement of the head, is rather small. Even more detrimental as concerns the obtaining of clear, sharp compound action potentials is the ensuing increase in the rise time of the acceleration impulse as transmitted to the vestibular labyrinth.

Figure 7:
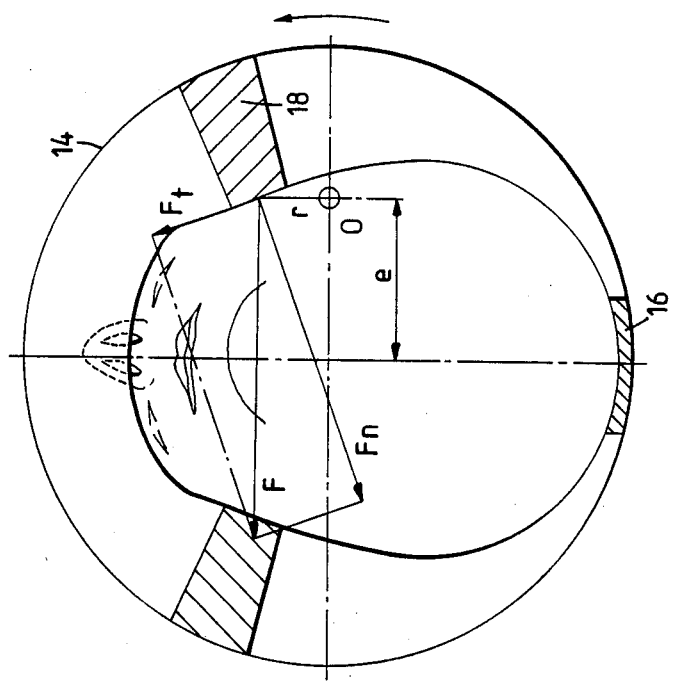
FIG. 7 illustrates the force acting on the head when the helmet is mounted eccentrically with respect to the motor shaft.

One way of overcoming this difficulty is to apply the clamping member 18 to a skull feature which is not perpendicular to the imaginary line connecting it with the center of rotation of the helmet 14. A solution to this problem is illustrated in FIG. 7, where it is seen that the center of rotation, O, is now off center with respect to the geometrical axis of the helmet 14 by a distance e for eccentricity. As a consequence, the normal force $F_n$ is now much larger, while the tangential force $F_t$ is much smaller. It will be remembered that the head holder according to the invention permits the helmet 14 to be operated in three positions (FIG. 2): a position of concentricity, in which the flange 12 is mounted on hole circle I, and two positions of eccentricity, in which flange 12 is mounted on hole circles II or III, with $e_{II} < e_{III}$.

Figure 8:
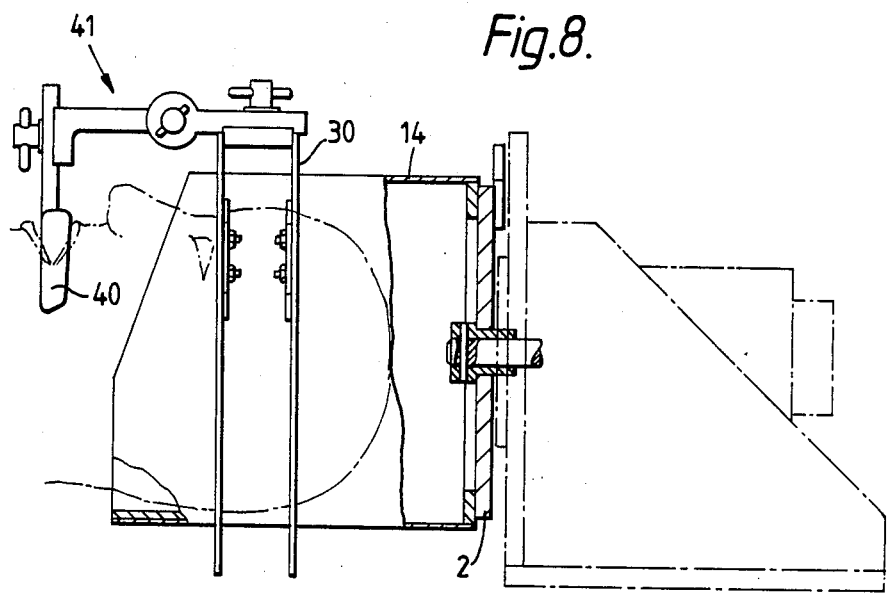
FIG. 8 shows another embodiment of the head holder, comprising a bite board.

Another solution, illustrated in FIG. 8, makes use of a so-called bite board 40, which is in fact a dental plate made of acrylic from a cast of the subject's upper teeth (or gums) prepared by a dentist. By means of a rigid, adjustable bracket 41, the bite board 40 is connected to the flanges 30 of the helmet 1. In this way the accelerating force is transmitted to the skull with minimal loss and delay, since the teeth are directly connected to the skull, with no intervening soft tissue. Thus, the rise time of the acceleration impulse, as transmitted to the vestibular labyrinth, is the shortest possible, enabling maximal synchronous activation of nerve fibers of the vestibular nerve.

So far, the only "head jerk" discussed was the angular jerk in the axial plane AP (FIG. 1) or, which is the same, about an axis perpendicular to this plane. However, to stimulate, and obtain evoked responses from, other receptors in the ear, it is necessary to apply the accelerative stimuli also in the coronal and the sagittal planes CP and SP, respectively.

Figure 9:
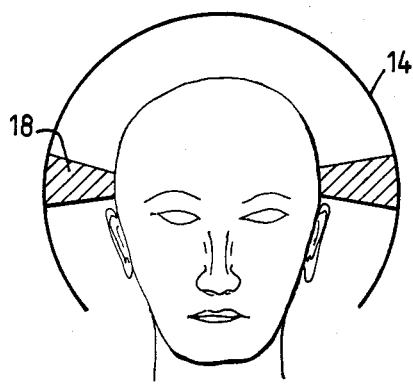
FIG. 9 is a schematic illustration of the head-holder set-up when used for angularly accelerating the head in the coronal plane.
Figure 10:
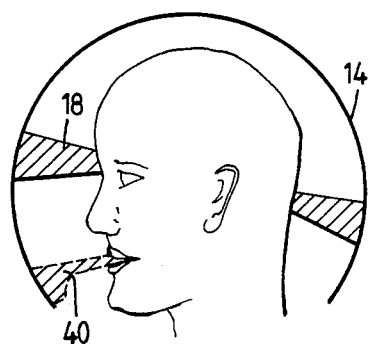
FIG. 10 shows the set-up of the head holder when used for angularly accelerating the head in the sagittal plane.

While tests in the axial plane AP are advantageously performed with the subject in the supine position, tests in the coronal or sagittal planes are performed with the subject sitting in a chair. Also, as can be seen from FIGS. 9 and 10, representing the head holder as used for angular acceleration in the coronal and sagittal planes respectively, the helmet 14 has to be partly open at its lower part, to permit introduction of the subject's head. It is either possible to provide two different helmets, one for the AP and another one for both the CP and SP tests, or also to design the AP helmet so that its lower portion can be removed.

While in the examination in the coronal plane, the clamping members 18 are again applied against the temporal bones (FIG. 9), in the SP examinations (FIG. 10) one clamping member 18 is applied to the head at, or near to, the occipital process at the back of the head, and the other one to the area including the glabella and the nasion. The latter clamping member can be replaced, or at least complemented, by the already mentioned bite board 40 which the subject holds between his teeth. The shape of the pressure pads of these clamping members 18 is of course modified to fit the specific shapes of the points of application.

With some locations, for instance the teeth or the occipital process in the SP-tests, or the teeth in the AP tests, it is possible to obtain good results also in the concentric mounting mode (I) of the helmet.

Figure 11:
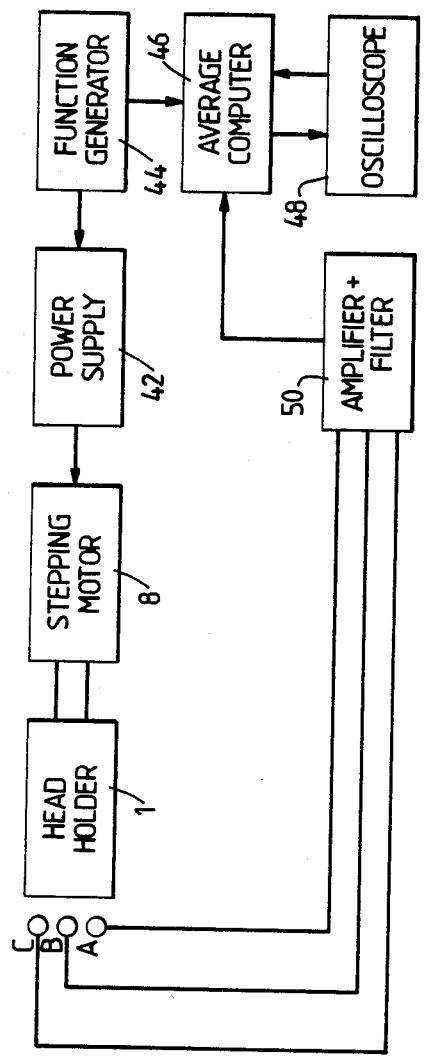
FIG. 11 is a block diagram relating the head holder to the driving and recording system.

In the block diagram of FIG. 11 there is seen the head holder 1 mechanically coupled to the output shaft of the stepping motor 8, the power supply 42 of which is controlled by a function generator 44 which also controls the sense of rotation of the stepping motor 8, as well as triggers the averaging computer 46. Leads from a ground electrode A, a scalp electrode B and a third electrode C, to be attached to the subject's external ear, or other appropriate locations, are led to an amplifier-filter unit 50, the output of which is fed to the averaging computer 46. Either the input signal of the computer 46 or its output signal can be displayed on the oscilloscope 48, from which the final average can be recorded photographically, or printed out on a suitable recorder.

Although the above-mentioned stepping motor has been found most suitable as a drive means, because of the easy controllability of both acceleration and amplitude, as well as the reproducibility of these magnitudes once set, other means of producing the required angular acceleration can be envisaged, such as, e.g., a solenoid of sufficient power, the linear working stroke of which is turned into a torque by an appropriate mechanical linkage, or a cockable and releasable spring similarly linked to the helmet.

Figure 12:
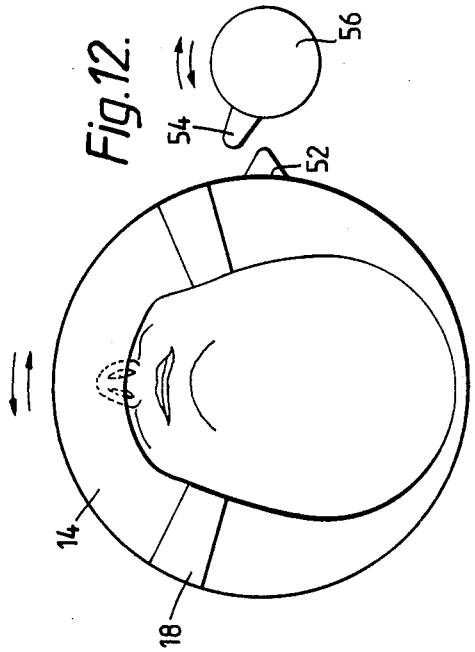
FIG. 12 illustrates another drive system for the head holder according to the invention.

Another drive system for the head holder according to the invention is shown in FIG. 12. A projection 52 is attached to the rotatably mounted helmet 14 and is impacted by a cam 54 mounted on the output member 56 of a power source. Depending on the sense of rotation of member 56, the helmet 14—and the subject's head inside the helmet —can be accelerated in the clockwise or counterclockwise sense.

While in the tests described, the subject's head was angularly accelerated in one (or about an axis perpendicular to one) of the three planes schematically illustrated in FIG. 1 (AP, CP and SP), the head holder according to the invention is envisaged to facilitate angular acceleration also in other planes. Such an arrangement would permit optimal stimulation also of the lateral semicircular canal which lies in a plane including with the AP an angle of about 30°.

For linear acceleration, the head holder 1 is somewhat modified inasmuch as it must now be movable in translation rather than in rotation. The same power sources that, in the previous embodiments, produced rotary motion, can also be used to produce linear motion, means of converting one type of motion into another being too well known to require a detailed treatment.

It should also be understood that the term "acceleration" as used in this specification is meant to include also deceleration (which can be interpreted as acceleration with a negative sign) producible, e.g., by braking.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. Apparatus for imparting to the head of a human subject accelerations useful in conducting physiological tests, the apparatus comprising:

a helmet-like member for at least partially surrounding the subject's head, said helmet-like member including flange means for mounting said helmet-like member;

a base member having a center of rotation; acceleration-imparting means for imparting to said base member rotational acceleration about the center of rotation of the base member;

means for mounting said flange means selectively on said base member in at least two different positions, at least one of which positions is eccentric with respect to the center of rotation of said base member; and head-clamping means mounted on said helmet-like member for engaging the head of a subject at selected locations to transfer to the head of the subject acceleration produced by said acceleration-imparting means.

2. The apparatus as claimed in claim 1, wherein said helmet-like member is further provided with at least one flange-like, radial projection fixedly attached to the outside of said helmet-like member and extending over at least part of the circumference thereof.

3. The apparatus as claimed in claim 2, wherein said helmet-like member is provided with two, spaced-apart, flange-like projections.

4. The apparatus as claimed in claim 1, wherein said head-clamping member comprises at least one pressure pad through which said accelerating force is transferred to said head.

5. The apparatus as claimed in claim 4, wherein said head-clamping means is further provided with two wing-like projections connected to said pad and passing through openings in said helmet-like member from the inside thereof to the outside thereof, said wing-like members being fixedly attachable, in selectable positions and orientations of said pad, to portions of said flange-like projections.

6. The apparatus as claimed in claim 5, wherein there are provided two head-clamping members, each comprising one pressure pad and two wing-like projections.

7. The apparatus as claimed in claim 1, wherein said helmet-like member has an inside surface with a portion for positioning adjacent the back of the head of a human subject and wherein a head rest is positioned on said portion.

8. The apparatus as claimed in claim 1 wherein said acceleration-imparting means is a stepping motor.

* * * * *